United States Patent
Fukui et al.

(10) Patent No.: US 9,897,491 B2
(45) Date of Patent: Feb. 20, 2018

(54) PROTECTING TUBE DETERIORATION DETECTING APPARATUS AND METHOD THEREFOR

(71) Applicant: Kobe Steel, Ltd., Hyogo (JP)

(72) Inventors: Toshihide Fukui, Kobe (JP); Chitaka Manabe, Kobe (JP); Eiji Takahashi, Kobe (JP); Yasuaki Yamane, Takasago (JP); Yusuke Tanaka, Takasago (JP)

(73) Assignee: Kobe Steel, Ltd., Hyogo (JP)

( * ) Notice: Subject to any disclaimer, the term of this patent is extended or adjusted under 35 U.S.C. 154(b) by 356 days.

(21) Appl. No.: 14/428,809

(22) PCT Filed: Oct. 7, 2013

(86) PCT No.: PCT/JP2013/005956
§ 371 (c)(1),
(2) Date: Mar. 17, 2015

(87) PCT Pub. No.: WO2014/076871
PCT Pub. Date: May 22, 2014

(65) Prior Publication Data
US 2015/0233849 A1    Aug. 20, 2015

(30) Foreign Application Priority Data

Nov. 15, 2012   (JP) ................. 2012-251008

(51) Int. Cl.
*G01K 1/08* (2006.01)
*G01K 7/02* (2006.01)
(Continued)

(52) U.S. Cl.
CPC .............. *G01K 7/026* (2013.01); *G01K 1/08* (2013.01); *G01K 7/02* (2013.01); *G01K 15/007* (2013.01); *G01N 27/18* (2013.01)

(58) Field of Classification Search
CPC ..................................................... G01K 7/026
See application file for complete search history.

(56) References Cited

U.S. PATENT DOCUMENTS

| 2,852,738 A | 9/1958 | Sherman |
| 5,828,567 A | 10/1998 | Eryurek et al. |

(Continued)

FOREIGN PATENT DOCUMENTS

| CN | 101576417 A | 11/2009 |
| JP | H08-313466 A | 11/1996 |

(Continued)

OTHER PUBLICATIONS

Hashemian et al ("New instrumentation Technologies for Testing the Bonding of Sensors to Solid Materials", NASA Contractor Report 4744, Aug. 1996, pp. 1-10, 18-58, 190-198, Appendix A and Appendix B).*

(Continued)

*Primary Examiner* — Clayton E Laballe
*Assistant Examiner* — Leon W Rhodes, Jr.
(74) *Attorney, Agent, or Firm* — Studebaker & Brackett PC

(57) ABSTRACT

A protecting tube deterioration detecting apparatus applies a predetermined electric current to a measurement target thermocouple with protecting tube for a predetermined time, calculates a temperature rise amount of the thermocouple, and determines, when the calculated temperature rise amount exceeds a predetermined threshold, that the protecting tube is deteriorated.

9 Claims, 5 Drawing Sheets

(51) Int. Cl.
*G01K 15/00* (2006.01)
*G01N 27/18* (2006.01)

(56) References Cited

U.S. PATENT DOCUMENTS

| | | | |
|---|---|---|---|
| 6,139,180 A | * | 10/2000 | Usher .................. G01K 7/026 374/1 |
| 6,556,145 B1 | | 4/2003 | Kirkpatrick et al. |
| 2008/0013598 A1 | | 1/2008 | Perotti et al. |

FOREIGN PATENT DOCUMENTS

| | | |
|---|---|---|
| JP | H09-218107 A | 8/1997 |
| JP | H11-330566 A | 11/1999 |
| JP | 2002-277333 A | 9/2002 |
| JP | 4084568 B2 | 4/2008 |
| JP | 2009-076533 A | 4/2009 |
| JP | 2011-059089 A | 3/2011 |
| KR | 20-0214689 Y1 | 2/2001 |

OTHER PUBLICATIONS

Cadwallader ("Reliability Estimates for Selected Sensors in Fusion Applications", Idaho National Engineering Laboratory Publication INEL-96/0295, Sep. 1996, sections 1 and 2).*
Yang et al ("A self-Validating thermocouple." IEEE Transactions on Control Systems Technology, vol. 5, No. 2, 1997, pp. 239-253., doi:10.1109/87.556028).*
The extended European search report issued by the European Patent Office dated May 20, 2016 which corresponds to European Patent Application No. 13855024.9-1555 and is related to U.S. Appl. No. 14/428,809.
International Search Report; PCT/JP2013/005956; dated Dec. 17, 2013.
Written Opinion of the International Searching Authority; PCT/JP2013/005956; dated Dec. 17, 2013.

* cited by examiner

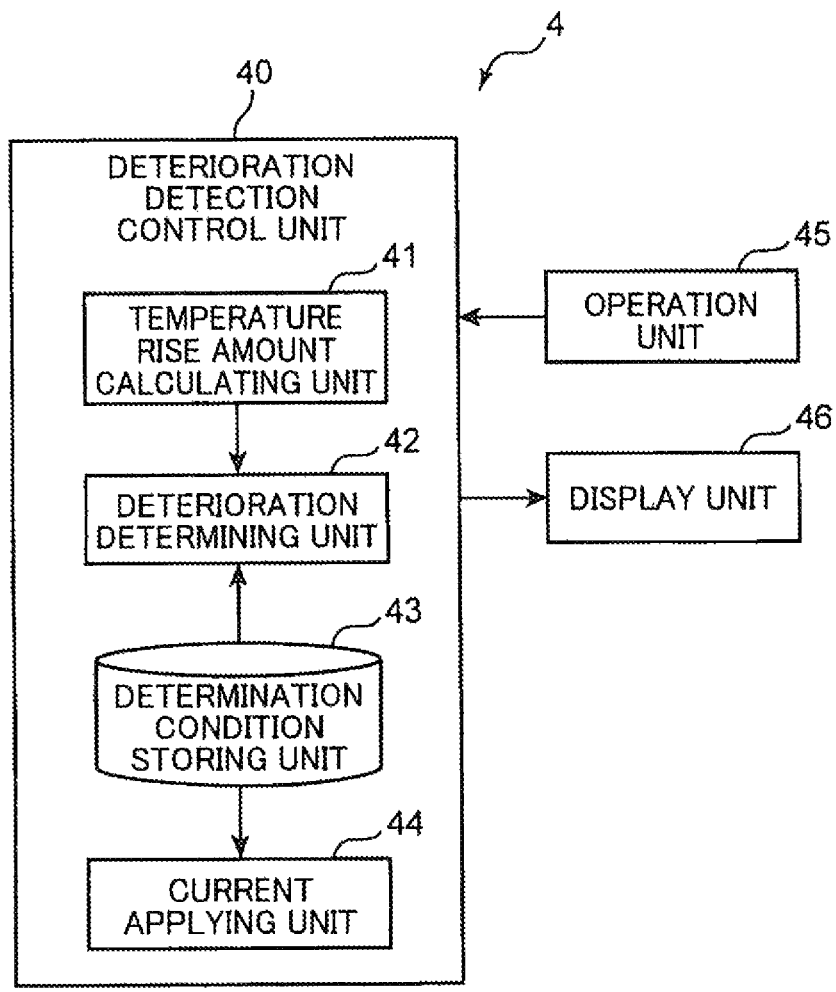

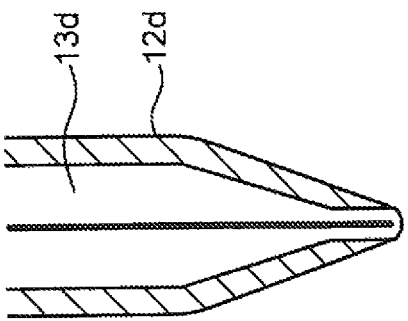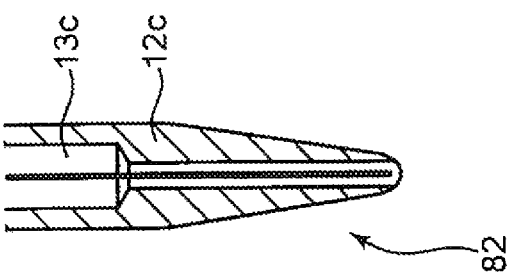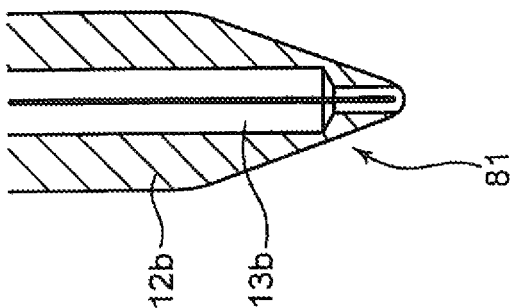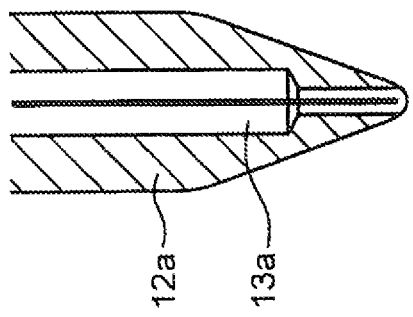

PROTECTING TUBE DETERIORATION DETECTING APPARATUS AND METHOD THEREFOR

BACKGROUND OF THE INVENTION

1. Field of the Invention

The present invention relates to a failure diagnosis technique for a protecting tube type thermocouple.

2. Background Art

A thermocouple has been often used as a thermometer for industrial purpose. Various thermocouples are used according to a range of temperature to be measured, a state of a measured place, required accuracy, and the like.

The thermocouple is also used for temperature measurement for a heating furnace and the like. When the thermocouple is used for a long time in such a high-temperature atmosphere and temperature rise and fall are repeated, it is likely that the thermocouple itself is deteriorated.

Therefore, there is proposed a technique for easily detecting and predicting deterioration of the thermocouple. For example, there is a technique for supplying an electric current to the thermocouple, measuring temperature from a thermoelectromotive force generated by the thermocouple, comparing a resistance value corresponding to temperature calculated from a relation between temperature stored in advance and a resistance value of the thermocouple and a resistance value of the thermocouple measured from a voltage fall at the time when the electric current is supplied to the thermocouple, and detecting deterioration of the thermocouple (see Japanese Patent Application Laid-Open No. H8-313466). There is also a technique for providing a first thermocouple close to a measurement target and a second thermocouple that is in close contact with the first thermocouple and farther away from the measurement target than the first thermocouple, comparing an output of the first thermocouple and an output of the second thermocouple, and determining, when an output difference between both the thermocouples exceeds a predetermined value, that the first thermocouple is deteriorated (see Japanese Patent Application Laid-Open No. H9-218107).

In kneading of a material having high viscosity such as rubber or plastic, sensing of a kneading state is important. The temperature of a kneaded object is measured as an index indicating the kneading state (a kneading degree). For such measurement of the temperature of the kneaded object, a protecting tube type thermocouple (a thermocouple with protecting tube) is often used. The protecting tube type thermocouple is a thermometer in which a thermocouple element wire is protected from the atmosphere of a measurement target by, for example, a protecting tube made of metal.

Since the temperature of the kneaded object serves as the index indicating the kneading degree in this way, when wear, bend, breakage, or the like occurs in the protecting tube during the kneading, it is necessary to replace the protecting tube as soon as possible. A problem could also occur in that broken pieces due to breakage or the like are mixed in a kneading material and adversely affect a product.

To prevent such a problem from occurring, it is sufficient if it is possible to confirm that the protecting tube is not deteriorated. In other words, it is sufficient if it is possible to detect deterioration such as wear or fracture of the protecting tube as soon as possible and appropriately ascertain replacement timing for the protecting tube.

SUMMARY OF THE INVENTION

The present invention is an invention devised in view of the above circumstances and it is an object of the present invention to provide a protecting tube deterioration detecting apparatus and a method therefor that can easily detect deterioration of a protecting tube of a protecting tube type thermocouple.

A protecting tube deterioration detecting apparatus according to an aspect of the present invention includes: a power supply unit configured to apply an electric current to a thermocouple with protecting tube; a temperature rise amount calculating unit configured to cause the power supply unit to apply a predetermined electric current to the thermocouple for a predetermined time and calculate a temperature rise amount of the thermocouple; and a deterioration determining unit configured to determine, when the temperature rise amount calculated by the temperature rise amount calculating unit exceeds a predetermined threshold, that the protecting tube is deteriorated.

BRIEF DESCRIPTION OF THE DRAWINGS

FIG. 3 is a functional block diagram of a deterioration detecting unit of the protecting tube deterioration detecting apparatus shown in FIG. 1;

FIG. 4 is a diagram showing an example of the configuration and contents of a determination condition table of the protecting tube deterioration detecting apparatus shown in FIG. 1;

FIGS. 8A to 8D are diagrams showing variations of protecting tube type thermocouples with improved responsiveness.

MODE FOR CARRYING OUT THE INVENTION

Figure 1:
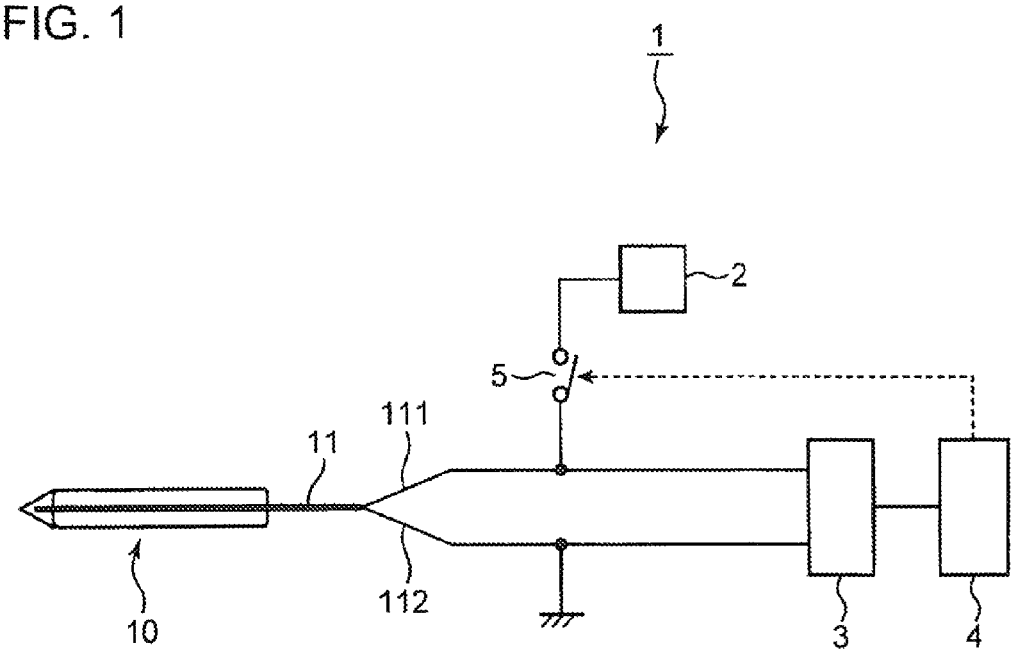
FIG. 1 is a diagram showing the configuration of a protecting tube deterioration detecting apparatus in an embodiment.

An embodiment according to the present invention is explained below on the basis of the drawings. Components denoted by the same reference numerals and signs in the figures are the same components. Explanation of the components is omitted as appropriate.

Embodiment

In kneading of a material having high viscosity such as rubber or plastic, the temperature of a kneaded object serves as an index indicating a kneading state (a kneading degree). Therefore, a thermometer configured to measure the temperature of the kneaded object is desired to have high accuracy and good responsiveness. As a method of improving measurement accuracy of temperature measured by a protecting tube type thermocouple and responsiveness, it is considered that, if the volume of a protecting tube is reduced, a heat capacity decreases and the responsiveness is improved.

However, when the volume of the protecting tube is reduced, for example, the thickness of the protecting tube is reduced, strength decreases. Therefore, it is more likely that wear, bend, breakage, and the like occur in the protecting tube during kneading. A problem could occur in that broken pieces due to breakage or the like are mixed in a kneading material and adversely affect a product.

To continue use of a protecting tube type thermocouple having high measurement accuracy for the temperature of a kneaded object and good responsiveness without causing such a problem, it is sufficient if it is possible to confirm that the protecting tube is not deteriorated. In other words, it is sufficient if it is possible to detect deterioration such as wear or fracture of the protecting tube as soon as possible and appropriately ascertain replacement timing for the protecting tube.

A protecting tube deterioration detecting apparatus according to an embodiment is a protecting tube deterioration detecting apparatus that easily detect a deterioration state of a protecting tube itself of a protecting tube type thermocouple. By inspecting the protecting tube type thermocouple at appropriate time using the protecting tube deteriorating detecting apparatus, it is possible to replace the protecting tube type thermocouple before deterioration advances or fracture or the like occurs. Therefore, it is possible to use the protecting tube type thermocouple with the thickness of the protecting tube reduced, measurement accuracy increased, and responsiveness improved.

<Configuration>

FIG. 1 is a diagram showing the configuration of a protecting tube deterioration detecting apparatus 1 according to the embodiment. A protecting tube type thermocouple 10 is an inspection target protecting tube type thermocouple (thermocouple with protecting tube). The protecting tube deterioration detecting apparatus 1 includes a power supply 2, a temperature detecting unit 3, a deterioration detecting unit 4, and a switch 5. A thermocouple 11 of the protecting tube type thermocouple 10 is configured by an element wire 111 and an element wire 112, each of which is connected to the temperature detecting unit 3. The temperature detecting unit 3 and the deterioration detecting unit 4 are connected to be capable of communicating with each other. The deterioration detecting unit 4 turns on and off the switch 5 and controls the power supply 2 to apply an electric current having desired amperage to the thermocouple 11 for a desired time.

The power supply 2 includes, for example, a DC/AC converter configured to convert a commercial alternating current into a direct current and generates a direct current having amperage designated by a current applying unit explained below.

Figure 2:
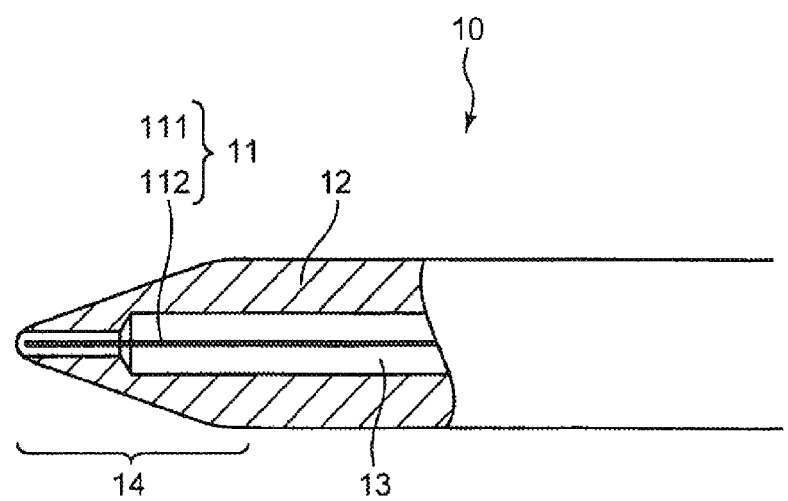
FIG. 2 is a sectional view of the distal end portion of a protecting tube type thermocouple of the protecting tube deterioration detecting apparatus shown in FIG. 1.

FIG. 2 is a sectional view of the distal end portion of the protecting tube type thermocouple 10. The protecting tube type thermocouple 10 includes the thermocouple 11 and a protecting tube 12. The element wires 111 and 112 configuring the thermocouple 11 are inserted through a hollow section 13 and joined in the distal end portion of the protecting tube 12. The protecting tube 12 is formed by, for example, stainless steel. Plating of chrome or the like is applied to the outer side of a conical section 14 at the distal end in thickness of, for example, about 0.1 mm (millimeter). Note that an insulating material may be filled in the hollow section 13. The element wires 111 and 112 may be covered with the insulating material.

In the thermocouple 11, a closed circuit is configured by joining both ends of the element wire 111 and the element wire 112, which are two metal wires of different types. When a temperature difference occurs at a contact of both the ends, a thermoelectromotive force is generated in the closed circuit and an electric current flows to the closed circuit.

The temperature detecting unit 3 measures the voltage of the thermoelectromotive force generated in the closed circuit. The temperature detecting unit 3 performs a calculation for converting the measured voltage into temperature and calculates temperature using a predetermined relation between the thermoelectromotive force and the temperature of the thermocouple 11 stored in an internal memory (not shown in the figure) in advance.

When the protecting tube type thermocouple 10 is used as a thermometer, the distal end portion of the protecting tube 12 is inserted into a kneaded object and brought into contact with the kneaded object, whereby heat is transmitted to the thermocouple 10. The temperature detecting unit 3 measures temperature from the voltage of generated thermoelectromotive force. That is, the protecting tube type thermocouple 10 and the temperature detecting unit 3 function as the thermometer. In this case, the temperature detecting unit 3 displays the calculated temperature on a predetermined display device (not shown in the figure) connected to the temperature detecting unit 3.

The deterioration detecting unit 4 performs determination concerning whether the protecting tube of the protecting tube type thermocouple 10 is deteriorated. Specifically, the deterioration detecting unit 4 detects a degree of deterioration of the protecting tube and determines whether the deterioration degree is in an allowable range. A functional block diagram of the deterioration detecting unit 4 is shown in FIG. 3. The deterioration detecting unit 4 is, for example, a personal computer configured to include a microprocessor, a peripheral circuit of the microprocessor, and the like. The deterioration detecting unit 4 functionally includes a deterioration detection control unit 40, an operation unit 45, and a display unit 46.

The operation unit 45 is a device configured to input a command for instructing the start of deterioration detection processing and various data necessary in performing the deterioration detection processing to the deterioration detecting unit 4. The operation unit 45 is, for example, a keyboard, a mouse, or a touch panel.

The display unit 46 is a device configured to display (output) a result of the deterioration detecting processing. The display unit 46 may output the command and the data input from the operation unit 45. The display unit 46 is a display device such as a CRT (Cathode Ray Tube) display, an LCD (Liquid Crystal Display), an organic EL (Electro Luminescence) display, and a plasma display.

The deterioration detection control unit 40 includes a temperature rise amount calculating unit 41, a deterioration determining unit 42, a current applying unit 44, and a determination condition storing unit 43 and controls the respective functional units included in the deterioration detecting unit 4 to perform the deterioration detection processing.

The current applying unit 44 controls the power supply 2 and turns on the switch 5 to apply a predetermined electric current to the thermocouple 11 for a predetermined time. A current amount to be applied and time of the current application are stored in the determination condition storing unit 43 as explained below.

The temperature rise amount calculating unit 41 acquires temperature from the temperature detecting unit 3 and calculates a rise amount of the temperature. Specifically, timing for acquiring temperature from the temperature detecting unit 3 is twice, i.e., before and after the current applying unit 44 applies the electric current to the thermocouple 11.

The deterioration determining unit 42 compares the temperature rise amount calculated by the temperature rise amount calculating unit 41 and a threshold stored in the determination condition storing unit 43 and determines deterioration of the protecting tube 12.

The determination condition storing unit 43 stores, in advance, data used when the deterioration detection processing is performed. In FIG. 4, a configuration example and a content example of a determination condition table 430 stored by the determination condition storing unit 43 are shown. The determination condition table 430 is stored in advance before the deterioration detection processing is performed. The determination condition table 430 is configured by a current item 431, an application time item 432, and a threshold item 433.

The current item 431 indicates an electric current (unit: ampere) applied to the protecting tube type thermocouple 10 set as an inspection target.

The application time item 432 indicates time (unit: second) in which the electric current indicated by the current item 431 is applied to the inspection target protecting tube type thermocouple 10.

The threshold item 433 indicates a threshold (unit: degree) of a temperature rise amount for determining that the protecting tube 12 is deteriorated when the electric current indicated by the current item 431 is applied to the inspection target protecting tube type thermocouple 10 for the time indicated by the application time item 432. A temperature rise amount obtained when the electric current indicated by the current item 431 is applied to the inspection target protecting tube type thermocouple 10 for the time indicated by the application time item 432 exceeds the threshold indicated by the threshold item 433, it is determined that the protecting tube 12 is deteriorated. That is, the threshold is an allowable value of the temperature rise amount.

<Deterioration Detecting Method>

A method of detecting deterioration of the protecting tube by the protecting tube deterioration detecting apparatus 1 is explained.

When an electric current flows to the thermocouple 11 of the protecting tube type thermocouple 10, the temperature of the distal end portion of the thermometer rises. There is a correlation between an amount of the temperature rise and a heat capacity of the distal end, i.e., a wear amount of the protecting tube 12. Therefore, the wear amount (a degree of deterioration) of the protecting tube 12 can be estimated from the temperature rise amount.

When an electric current is applied to the thermocouple 11 of the protecting tube type thermocouple 10, the distal end of the thermocouple 11 generates heat. The generated heat diffuses to the distal end portion of the protecting tube type thermocouple 10 and raises temperature. A wear amount of the protecting tube 12 is determined on the basis of an amount of the temperature rise.

First, a predetermined current is applied to the thermocouple 11 of the protecting tube type thermocouple 10 in which the protecting tube 12 is not deteriorated (worn) for a predetermined time, and a temperature rise amount is calculated. A threshold for determining deterioration is determined from the calculated temperature rise amount, and is stored in the determination condition storing unit 43.

Then the predetermined electric current is applied to the thermocouple 11 of the measurement target protecting tube type thermocouple 10 for the predetermined time and a temperature rise amount is calculated in the same manner as the application to the protecting tube type thermocouple 10 in which the protecting tube 12 is not deteriorated. The calculated temperature rise amount is compared with the threshold stored in the determination condition storing unit 43, and it is determined whether the protecting tube 12 is deteriorated.

A difference between the temperature rise amount of the measurement target protecting tube type thermocouple 10 and the temperature rise amount of the protecting tube type thermocouple 10 in which the protecting tube 12 is not deteriorated indicates a decrease amount of the volume of the distal end portion of the protecting tube 12, i.e., a deterioration degree (a wear amount) of the protecting tube 12. If the protecting tube 12 is normal, i.e., wear of the protecting tube 12 is small, the temperature rise amount is small. However, as the deterioration degree increases, the temperature rise amount increases.

Therefore, the deterioration degree of the protecting tube 12 of the inspection target protecting tube type thermocouple 10 is determined using the difference between the temperature rise amounts indicating an allowable deterioration degree (wear amount). Specifically, when the difference between the temperature rise amount of the inspection target protecting tube type thermocouple 10 and the temperature rise amount of the protecting tube type thermocouple 10 in which the protecting tube 12 is not deteriorated exceeds this difference between the temperature rise amounts indicating the allowable deterioration degree, it is determined that the deterioration of the protecting tube 12 of the inspection target protecting tube type thermocouple 10 is deterioration in an unallowable degree.

Figure 6:
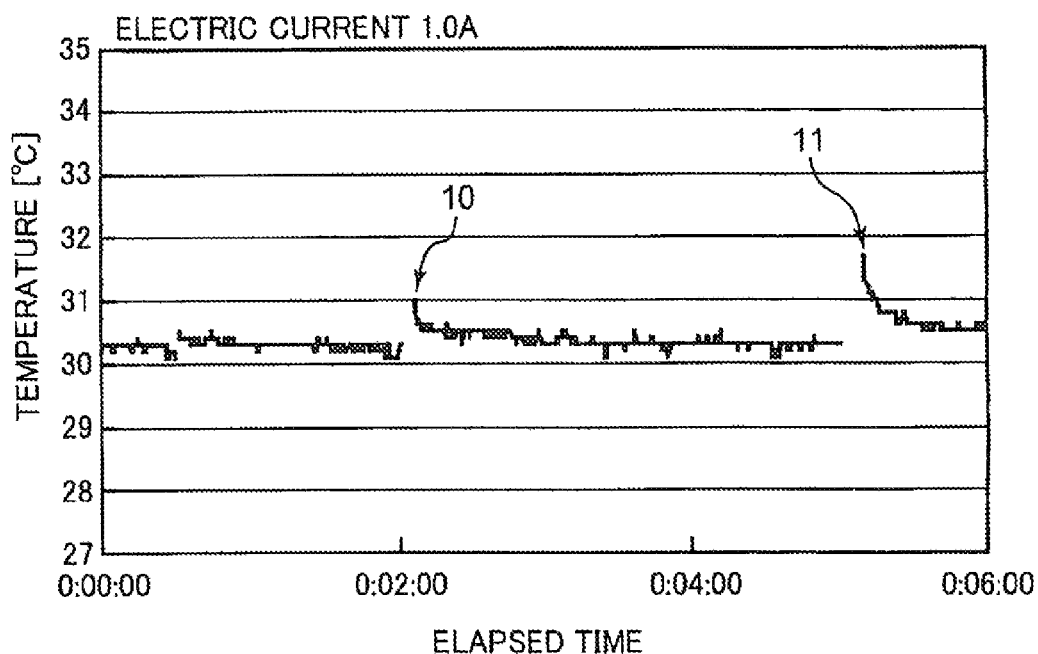
FIG. 6 is a diagram for explaining a method of the deterioration detection processing of the protecting tube deterioration detecting apparatus shown in FIG. 1.
Figure 7:
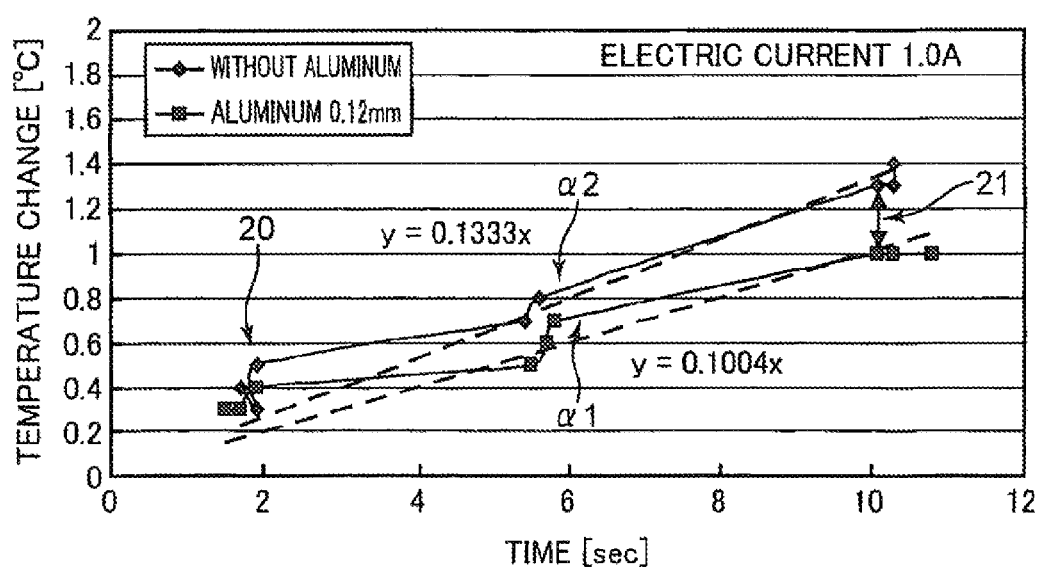
FIG. 7 is a diagram for explaining the method of the deterioration detection processing of the protecting tube deterioration detecting apparatus shown in FIG. 1.

In FIGS. 6 and 7, a result of an experiment performed by attaching aluminum foil having thickness of about 0.12 mm (millimeter) to the distal end portion of the protecting tube type thermocouple 10 and simulating presence or absence of wear is shown. The aluminum foil is assumed to be plating applied to the outer side of the conical section 14 at the distal end of the protecting tube 12. That is, when the aluminum foil is not attached, a state in which the plating peels and the protecting tube 12 is worn is shown.

FIG. 6 is a graph of a temperature measurement result obtained when an electric current of 1 A is applied to a protecting tube type thermocouple not attached with aluminum foil. In FIG. 6, the abscissa indicates an application time represented in minute units and the ordinate indicates temperature represented in degree (° C.) units. The temperature on the ordinate is temperature measured by the temperature detecting unit 3.

For example, when the electric current of 1 A was applied to the protecting tube type thermocouple for 2 seconds, about 31 degrees was measured (see an arrow 10). When the electric current of 1 A was applied for 5.5 seconds, about 31.5 degrees was measured (see an arrow 11). The same temperature measurement is performed for a protecting tube type thermocouple attached with aluminum foil.

FIG. 7 is a graph for explaining a change in a temperature rise amount obtained when the electric current of 1 A is applied to the protecting tube type thermocouple. In FIG. 7, the abscissa indicates an application time represented in second units and the ordinate indicates a temperature change (a temperature rise amount) represented in degree (° C.) units. The temperature change amount on the ordinate is a temperature change amount obtained when an electric current is applied for seconds indicated by the abscissa. A graph α1 is a graph indicating a transition of a temperature rise amount obtained when the electric current of 1 A is applied to the protecting tube type thermocouple attached with the aluminum foil. A graph α2 is a graph indicating a transition of a temperature rise amount obtained when the electric current 1 A is applied to the protecting tube type thermocouple from which the aluminum foil is detached. Graphs indicated by dotted lines are respectively linear approximate curves of the graph α1 and the graph α2.

For example, when temperature measured when the electric current of 1 A is applied for 2 seconds is 31 degrees (see the arrow 10 in FIG. 6) and temperature measured by the temperature detecting unit 3 before the electric current is applied is 30.5 degrees, a temperature change amount 0.5 degree is a temperature rise amount (see an arrow 20 in FIG. 7).

In FIG. 7, when the electric current of 1 A is fed for 10 seconds, in the protecting tube type thermocouple from which the aluminum foil is detached, a change in the temperature raise amount of about 0.2 degree is seen compared with the protecting tube type thermocouple attached with the aluminum foil (see an arrow 21). Specifically, the temperature change (the ordinate) at the time when the application time (the abscissa) in the graph α1 is 10 seconds is about 1.0 degree. The temperature change (the ordinate) at the time when the application time (the abscissa) in the graph α2 is 10 seconds is about 1.25 degrees. The graph α1 is a graph indicating a transition of the temperature rise amount of the protecting tube type thermocouple attached with the aluminum foil. The graph α2 is a graph indicating a transition of the temperature rise amount of the protecting tube type thermocouple from which the aluminum foil is detached. Therefore, the temperature rise amount of the protecting tube type thermocouple from which the aluminum foil is detached is about 0.2 degree higher than the temperature rise amount of the protecting tube type thermocouple attached with the aluminum foil.

Since the aluminum foil is compared to the plating, the protecting tube type thermocouple from which the aluminum foil is detached can be considered a protecting tube type thermocouple worn by an amount equivalent to the thickness of the aluminum foil, i.e., on which the plating having thickness of about 0.1 mm is worn (peeled). Therefore, the temperature rise amount is 0.2 degree higher in the protecting tube type thermocouple on which the plating is worn.

For example, when deterioration of a protecting tube of a protecting tube type thermocouple, the thickness of allowable wear of which is 0.1 mm and which measures the temperature of a kneaded object, is detected, at a stage when the kneaded object is discharged (because, during kneading, temperature changes according to presence or absence of contact of a kneading target and the thermometer), the protecting tube deterioration detecting apparatus 1 applies the electric current of 1 A to the protecting tube type thermocouple for 10 seconds and measures a temperature rise amount. When the temperature rise amount is compared with a temperature rise amount of the protecting tube type thermocouple in an initial state, which is a state in which the protecting tube type thermocouple is not deteriorated, if a difference is equal to or larger than 0.2 degree, the protecting tube deterioration detecting apparatus 1 determines that a wear amount is 0.1 mm. The protecting tube type thermocouple (the thermometer) is replaced. For example, when the temperature rise amount of the protecting tube type thermocouple in the initial state is "1.0" degree, if the temperature rise amount of the inspection target protecting tube type thermocouple exceeds "1.2" degrees obtained by adding "0.2" degree to 1.0 degree, the protecting tube type thermocouple is replaced.

In this case, the determination condition table 430 in which "1" ampere is set as the current item 431, "10" seconds is set as the application time item 432, and "1.2" degrees is set as the threshold item 433 is stored in the determination condition storing unit 43.

The process for measuring a temperature rise amount may be performed several times rather than only once to estimate a deterioration degree.

Besides setting the temperature rise amount of the protecting tube type thermocouple as the threshold as explained above, the tilts of the linear approximate curves of the graphs α1 and α2 indicated by the dotted lines in FIG. 7 may be used. For example, in FIG. 7, the linear approximate curve of the graph α1 of the protecting tube type thermocouple attached with the aluminum foil is indicated by y=0.1004x. The linear approximate curve of the graph α2 of the protecting tube type thermocouple from which the aluminum foil is detached is indicated by y=0.1333x. That is, the tilt of the linear approximate curve is larger in the graph α2 than the graph α1. That is, the tilt of the graph of the protecting tube type thermocouple in which the protecting tube is deteriorated is large compared with the tilt of the graph of the protecting tube type thermocouple in which the protecting tube is not deteriorated. Therefore, when the tilt of the linear approximate curve is set as the threshold and, for example, when the tilt exceeds "0.1333", it may be determined that the protecting tube is deteriorated.

<Operation>

Figure 5:
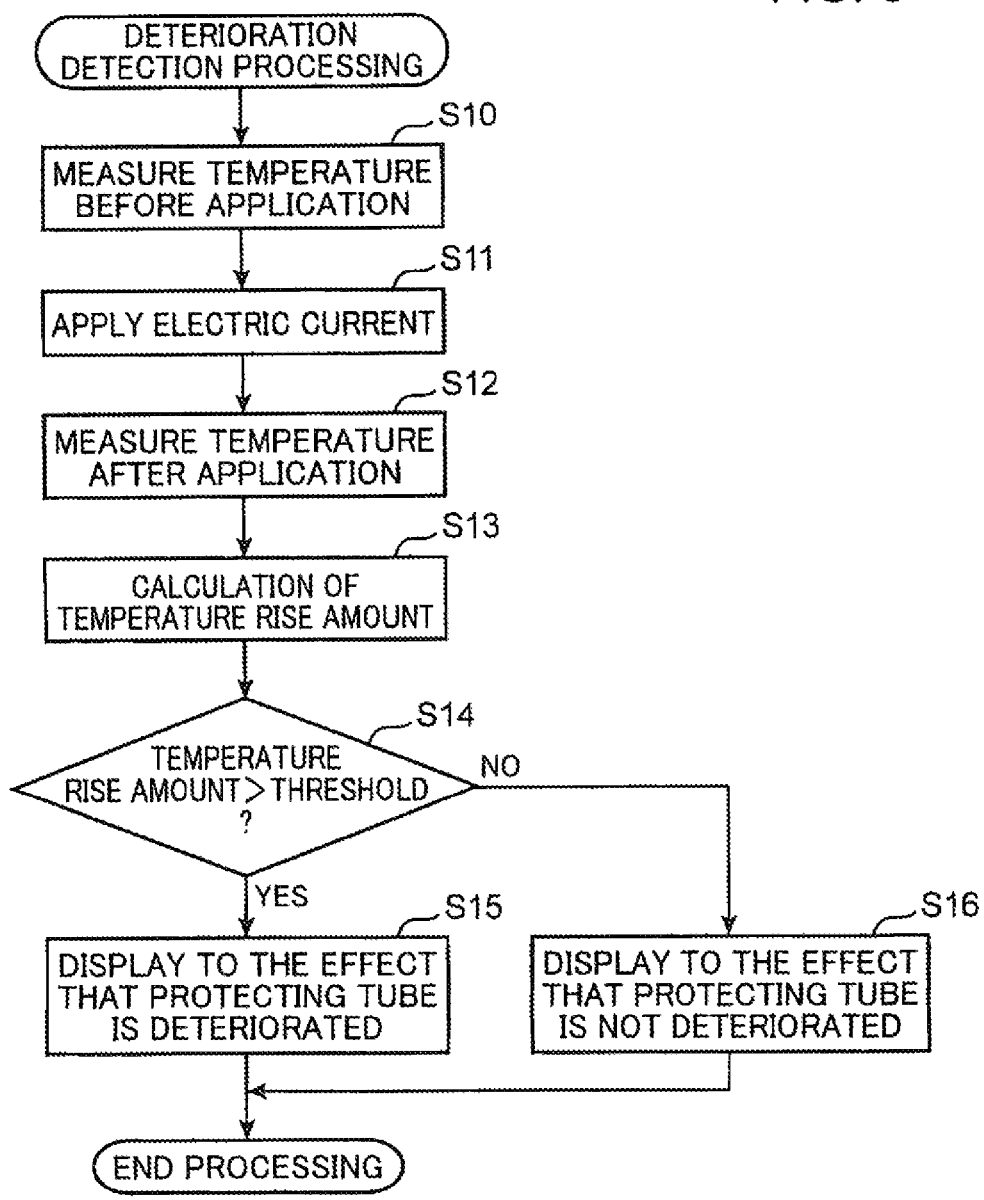
FIG. 5 is a flowchart of deterioration detection processing of the protecting tube deterioration detecting apparatus shown in FIG. 1.

The operation of the protecting tube deterioration detecting apparatus 1 is explained with reference to FIG. 5. FIG. 5 is a flowchart of the deterioration detection processing by the protecting tube deterioration detecting apparatus 1.

First, a user connects the inspection target protecting tube type thermocouple 10 to the protecting tube deterioration detecting apparatus 1 and operates the operation unit 45 of the deterioration detecting unit 4 to input a command for instructing the start of the deterioration detection processing. Note that it is assumed that the determination condition table 430 (see FIG. 4) is stored in the determination condition storing unit 43 in advance.

The temperature rise amount calculating unit 41, which detects via the deterioration detection control unit 40 that the operation unit 45 is operated and the command is input, instructs the temperature detecting unit 3 to perform temperature measurement.

The temperature detecting unit 3, which receives the instruction, measures the temperature of the protecting tube type thermocouple 10 and passes the measured temperature to the temperature rise amount calculating unit 41 (step S10). The temperature rise amount calculating unit 41, to which the temperature is passed, stores the passed temperature in a work area as temperature before current application.

Subsequently, the current applying unit 44 refers to the determination condition table 430 stored in the determination condition storing unit 43 and reads out the value "1" of the electric current having the amperage set as the current item 431 and the time "10" set as the application time item 432. The current applying unit 44 turns on the switch 5 and controls the power supply 2 to apply the electric current of "1" ampere to the thermocouple 11 for "10" seconds (step S11).

After the application of the electric current to the thermocouple 11, the temperature rise amount calculating unit 41 instructs the temperature detecting unit 3 to perform temperature measurement.

The temperature detecting unit 3, which receives the instruction, measures the temperature of the protecting tube type thermocouple 10 and passes the measured temperature to the temperature rise amount calculating unit 41 (step S12). The temperature rise amount calculating unit 41, to which the temperature is passed, calculates, as a temperature rise amount, a difference between the passed temperature and the temperature before the current application stored in the work area (step S13). The temperature rise amount calculating unit 41 passes the calculated temperature rise amount to the deterioration determining unit 42.

The deterioration determining unit 42, to which the temperature rise amount is passed from the temperature rise amount calculating unit 41, reads out the threshold "1.2" degrees set as the threshold item 433 from the determination condition table 430 of the determination condition storing unit 43. The deterioration determining unit 42 compares the temperature rise amount passed from the temperature rise amount calculating unit 41 and the threshold. When the temperature rise amount is larger than the threshold, the deterioration determining unit 42 determines that the protecting tube 12 of the protecting tube type thermocouple 10 is deteriorated (step S14: YES), causes, via the deterioration detection control unit 40, the display unit 46 to display to the effect that the protecting tube 12 is deteriorated (step S15), and ends the processing. On the other hand, when the temperature rise amount is equal to or smaller than the threshold, the deterioration determining unit 42 determines that a degree of deterioration of the protecting tube 12 of the protecting tube type thermocouple 10 is in an allowable range (step S14: NO), causes, via the deterioration detection control unit 40, the display unit 46 to display to the effect that the protecting tube 12 is not deteriorated (step S16), and ends the processing.

Since a deterioration degree of the protecting tube 12 can be easily determined in this way, it is possible to learn accurate replacement timing for the thermometer. That is, since the thermometer can be replaced at an appropriate timing, an adverse effect on processing content of a manufacturing process and a process due to fracture is eliminated.

<Variations of Protecting Tube Type Thermocouples>

As explained above, the protecting tube deterioration detecting apparatus 1 makes it possible to easily perform detection of deterioration of the protecting tube. Therefore, it is possible to frequently inspect a degree of deterioration due to a state of, for example, plating peeling of the protecting tube of the protecting tube type thermocouple. That is, it is possible to easily estimate, at appropriate time, the life of the protecting tube type thermocouple functioning as a thermometer. Therefore, it is possible to replace the protecting tube type thermocouple at appropriate timing. Therefore, it is possible to adopt a protecting tube having a small volume (a small thickness), which is highly likely to be worn or fractured and is difficult to be practically used in the past. As a result, it is possible to realize a thermometer excellent in responsiveness.

Variations of protecting tube type thermocouples are shown in FIGS. 8A to 8D. In FIGS. 8A to 8D, sectional views of the distal end portions of the protecting tube type thermocouples are shown. FIG. 8A shows the shape of the distal end portion of a protecting tube type thermocouple in the past. FIGS. 8B, 8C, and 8D show examples of the shapes of the distal end portions of protecting tube type thermocouples that realize temperatures excellent in responsiveness.

In the protecting tube type thermocouples shown in FIGS. 8B, 8C, and 8D, the volume of the protecting tube 12 is small compared with the protecting tube type thermocouple in the past shown in FIG. 8A. Therefore, a heat capacity of the protecting tube decreases and a thermometer with good responsiveness can be realized.

Specifically, a hollow section 13b of the protecting tube type thermocouple shown in FIG. 8B expands further to the distal end portion compared with a hollow section 13a of the protecting tube type thermocouple shown in FIG. 8A (see an arrow 81). Therefore, the volume of a protecting tube 12b around the distal end (a joining section) of a thermocouple, which generates heat, is small compared with a protecting tube 12a in the past.

A protecting tube 12c of the protecting tube type thermocouple shown in FIG. 8C is thin compared with the protecting tube 12a of the protecting tube type thermocouple shown in FIG. 8A. As a result, the thickness of the protecting tube 12c decreases (see an arrow 82) and a hollow section 13c is separated from the distal end. Therefore, the thickness of the protecting tube 12c at the distal end portion is small compared with the protecting tube 12a in the past. The thickness around the distal end of the thermocouple is small and heat is easily transmitted.

A protecting tube 12d of the protecting tube type thermocouple shown in FIG. 8D has the same thickness as the protecting tube 12a of the protecting tube type thermocouple shown in FIG. 8A. However, the thickness of the protecting tube 12d is small. That is, a hollow section 13d is wider than the hollow section 13a in the past and is inclined such that the thickness of the protecting tube 12d decreases at the distal end portion. Therefore, the volume of the protecting tube 12d at the distal end portion is small compared with the protecting tube 12a in the past.

By reducing the volume of the protecting tube 12 as shown in FIGS. 8B to 8D, when deterioration of the protecting tube is detected by the protecting tube deterioration detecting apparatus 1, a more precise wear amount inspection can be performed. This is because, when the same electric current is applied for the same time to respective two protecting tube type thermocouple having different volumes of the protecting tube 12, the protecting tube type thermocouple having a smaller volume of the protecting tube 12 has a larger temperature rise amount. For example, protecting tube type thermocouples in which wear amounts of the protecting tube 12 having a large volume and the protecting tube 12 having a small volume are the same are assumed. When a difference between temperature rise amounts of the respective protecting tube type thermocouples in which the protecting tubes 12 are worn and a difference between temperature rise amounts of the not-worn protecting tubes 12 of the respective protecting tube type thermocouples are calculated, the difference is larger in the protecting tube 12 having the small volume. Therefore, when rise amounts of temperatures are measured in the same manner, a more precise wear amount can be detected when the volume of the protecting tube 12 is smaller.

In this embodiment, the threshold item 433 is stored in the determination condition storing unit 43 in advance. When the temperature rise is larger than the threshold, it is determined that the protecting tube is deteriorated. The display to the effect that the protecting tube is deteriorated is performed. However, even when the temperature rise amount is equal to or smaller than the threshold, a deterioration degree may be determined according to a difference between the temperature rise amount and the threshold. The deterioration degree is, for example, "deterioration degree 50%" and "deterioration degree 10%". A message corresponding to the deterioration degree may be displayed. The message is, for example, "Time for replacement will come soon," and "Please inspect frequently."

In the embodiment, the temperature of the thermocouple is detected before the application of the electric current to the protecting tube type thermocouple is started and after the electric current is applied for the predetermined time. However, temperature may be detected during the application of the electric current and detected again a predetermined time after the point of the detection.

In the embodiment, the protecting tube type thermocouple is explained as the example. However, for a thermocouple attached with some kind of cover for protecting an element wire such as a sheath thermocouple, detection of deterioration can be performed by the protecting tube deterioration detecting apparatus in this embodiment.

This specification discloses the techniques of the various forms as explained above. Among the techniques, main techniques are summarized below.

A protecting tube deterioration detecting apparatus according to an aspect of the present invention includes: a power supply unit configured to apply an electric current to a thermocouple with protecting tube; a temperature rise amount calculating unit configured to cause the power supply unit to apply a predetermined electric current to the thermocouple for a predetermined time and calculate a temperature rise amount of the thermocouple; and a deterioration determining unit configured to determine, when the temperature rise amount calculated by the temperature rise amount calculating unit exceeds a predetermined threshold, that the protecting tube is deteriorated.

A protecting tube deterioration detecting method according to another aspect of the present invention is a protecting tube deterioration detecting method for a thermocouple with protecting tube, including: a temperature rise amount calculating step of applying a predetermined electric current to the thermocouple for a predetermined time and calculating a temperature rise amount of the thermocouple; and a deterioration determining step of determining, when the temperature rise amount exceeds a predetermined threshold, that the protecting tube is deteriorated.

With the protecting tube deterioration detecting apparatus and the protecting tube deterioration detecting method having such a configuration, when the predetermined electric current is applied to an inspection target thermocouple with protecting tube (protecting tube type thermocouple) for a predetermined time, it is possible to determine deterioration of the protecting tube by calculating a temperature rise amount of the thermocouple. The deterioration of the protecting tube means that plating peels and the volume of the protecting tube decreases because of wear, fracture, or the like.

A degree of deterioration (a wear amount) of the protecting tube can be easily inspected by the protecting tube deterioration detecting apparatus according to the present invention. Therefore it is possible to inspect a degree of deterioration of the protecting tube frequently, for example, every time measurement of temperature is performed by the protecting tube type thermocouple. That is, it is possible to estimate the life of the protecting tube type thermocouple (a thermometer) according to a state of the deterioration of the protecting tube and perform replacement of the thermometer at appropriate timing. Since the thermometer can be replaced at the appropriate timing, it is possible to perform appropriate temperature management in processing in a manufacturing process. Further, it is possible to prevent an adverse effect on a product such as mixing of broken pieces or the like due to fracture.

It is possible to simply and accurately determine deterioration of the protecting tube and easily find fracture or the like of the protecting tube. Therefore, it is possible to adopt a protecting tube type thermocouple in which a protecting tube having a small volume (small thickness), which has a risk of fracture and is difficult to be practically used in the past, is used. That is, it is possible to create and use a protecting tube type thermocouple with improved responsiveness of temperature measurement.

It is preferable that the protecting tube deterioration detecting apparatus further includes a temperature detecting unit configured to detect temperature from a thermoelectromotive force generated by the thermocouple, and the temperature rise amount calculating unit causes the temperature detecting unit to detect respective temperatures before and after the application of the electric current to the thermocouple and calculates the temperature rise amount on the basis of the detected temperatures.

With this configuration, the temperatures are detected before the predetermined electric current is applied for the predetermined time and after the predetermined current is applied. Therefore, it is possible to surely detect a change in the temperature of the thermocouple.

It is preferable that the protecting tube deterioration detecting apparatus further includes a temperature detecting unit configured to detect temperature from a thermoelectromotive force generated by the thermocouple, and the temperature rise amount calculating unit causes, after causing the power supply unit to start the application of the electric current to the thermocouple, the temperature detecting unit to detect temperature, causes, when a predetermined time elapses after the detection, the temperature detecting unit to detect temperature again, and calculates the temperature rise amount on the basis of the respective detected temperatures.

With this configuration, even while the predetermined electric current is applied, it is possible to detect a change in the temperature of the thermocouple.

It is preferable that the protecting tube deterioration detecting apparatus further includes a temperature detecting unit configured to detect temperature from a thermoelectromotive force generated by the thermocouple, and the temperature rise amount calculating unit causes, after causing the power supply unit to start the application of the electric current to the thermocouple, the temperature detecting unit to detect the temperature of the thermocouple a plurality of times and calculates a temperature rise ratio of the thermocouple as the temperature rise amount from a plurality of the detected temperatures.

With this configuration, if the temperature of the thermocouple is detected a plurality of times at arbitrary points of time, it is possible to calculate the temperature rise ratio as the temperature rise amount.

It is preferable that, in the protecting tube deterioration detecting apparatus, the predetermined threshold is an allowable value of the temperature rise amount calculated on the basis of the temperature rise amount obtained when the predetermined electric current is applied for the predetermined time to the thermocouple in which the protecting tube is not deteriorated.

With this configuration, an allowable value based on the thermocouple in which the protecting tube is not deteriorated is used, thereby enabling deterioration of the protecting tube to be surely detected.

It is preferable that the protecting tube deterioration detecting apparatus further includes: a switch connected between one element wire of the thermocouple and the power supply unit; and a current applying unit configured to turn on the switch for the predetermined time.

With this configuration, it is possible to surely apply the predetermined current to the thermocouple during the predetermined time.

It is preferable that the protecting tube deterioration detecting apparatus further includes a determination condition storing unit configured to store a determination condition table in which the predetermined current, the predetermined time, and the predetermined threshold are associated with one another, and the current applying unit determines the predetermined time, the predetermined current, and the predetermined threshold by referring to the determination condition table.

With this configuration, it is possible to easily change a condition for detecting deterioration of the thermocouple simply by rewriting the determination condition table. That is, it is possible to detect deterioration of protecting tubes of various thermocouples simply by rewriting the determination condition table according to a specification of a detection target thermocouple with protecting tube.

It is preferable that the protecting tube deterioration detecting apparatus further includes a display unit, and the deterioration determining unit calculates a deterioration degree on the basis of the temperature rise amount calculated by the temperature rise amount calculating unit and the predetermined threshold and causes the display unit to display the calculated deterioration degree.

With this configuration, a user can easily learn a deterioration degree of the protecting tube of the detection target thermocouple.

As described above, the protecting tube deterioration detecting apparatus according to the present invention can easily detect deterioration of the protecting tube of the protecting tube type thermocouple.

This application is based on Japanese Patent Application No. 2012-251008 filed on Nov. 15, 2012, the contents of which are included in this application.

To represent the preset invention, the present invention is appropriately and sufficiently explained above through the embodiment with reference to the drawings. However, it should be recognized that those skilled in the art can easily change and/or improve the embodiment. Therefore, as long as a change form or an improvement form carried out by those skilled in the art is not in a level departing from the scope of rights of claims described in the scope of claims, the change form or the improvement form is interpreted as being included in the scope of rights of the claims.

What is claimed is:

1. A protecting tube deterioration detecting apparatus, comprising:
    a power supply unit configured to apply an electric current to a thermocouple with protecting tube having a distal end to which plating is applied to form a plating layer with a predetermined thickness;
    a temperature rise amount calculator configured to cause the power supply unit to apply a predetermined electric current to the thermocouple for a predetermined time and calculate a temperature rise amount of the thermocouple; and
    a deterioration determinator configured to determine a wear amount of the plating layer of the protecting tube based on the temperature rise amount calculated by the temperature rise amount calculator.

2. The protecting tube deterioration detecting apparatus according to claim 1, further comprising a temperature detecting unit configured to detect temperature from a thermoelectromotive force generated by the thermocouple, wherein
    the temperature rise amount calculator causes the temperature detecting unit to detect temperatures before and after the application of the electric current to the thermocouple and calculates the temperature rise amount on the basis of the detected temperatures.

3. The protecting tube deterioration detecting apparatus according to claim 1, further comprising a temperature detecting unit configured to detect temperature from a thermoelectromotive force generated by the thermocouple, wherein
    the temperature rise amount calculator causes, after causing the power supply unit to start the application of the electric current to the thermocouple, the temperature detecting unit to detect temperature, causes, when a predetermined time elapses after the detection, the temperature detecting unit to detect temperature again, and calculates the temperature rise amount on the basis of the respective detected temperatures.

4. The protecting tube deterioration detecting apparatus according to claim 1, further comprising a temperature detecting unit configured to detect temperature from a thermoelectromotive force generated by the thermocouple, wherein
    the temperature rise amount calculator causes, after causing the power supply unit to start the application of the electric current to the thermocouple, the temperature detecting unit to detect temperature of the thermocouple a plurality of times and calculates a temperature rise ratio of the thermocouple as the temperature rise amount from a plurality of the detected temperatures.

5. The protecting tube deterioration detecting apparatus according to claim 1, wherein
    the predetermined threshold is an allowable value of the temperature rise amount calculated on the basis of the temperature rise amount obtained when the predetermined electric current is applied for the predetermined time to the thermocouple in which the protecting tube is not deteriorated.

6. The protecting tube deterioration detecting apparatus according to claim 1, further comprising:
    a switch connected between one element wire of the thermocouple and the power supply unit; and
    a current applying unit configured to turn on the switch for the predetermined time.

7. The protecting tube deterioration detecting apparatus according to claim 6, further comprising a determination condition storage configured to store a determination condition table in which the predetermined current, the predetermined time, and the predetermined threshold are associated with one another, wherein
    the current applying unit determines the predetermined time, the predetermined current, and the predetermined threshold by referring to the determination condition table.

8. The protecting tube deterioration detecting apparatus according to claim 1, further comprising a display unit, wherein
    the deterioration determinator calculates a deterioration degree on the basis of the temperature rise amount calculated by the temperature rise amount calculating unit and the predetermined threshold and causes the display unit to display the calculated deterioration degree.

9. A protecting tube deterioration detecting method for a thermocouple with protecting tube having a distal end to which plating is applied to form a plating layer with a predetermined thickness, said method comprising:
- a temperature rise amount calculating step of applying a predetermined electric current to the thermocouple for a predetermined time and calculating a temperature rise amount of the thermocouple; and
- a deterioration determining step of determining a wear amount of the plating layer of the protecting tube based on the temperature rise amount of the thermocouple.

* * * * *